United States Patent [19]

Brush

[11] Patent Number: 5,583,236
[45] Date of Patent: * Dec. 10, 1996

[54] FLUORESCEIN LABELLED PHOSPHORAMIDITES

[75] Inventor: Charles K. Brush, Whitefish Bay, Wis.

[73] Assignee: Pharmacia Biotech Inc., Milwaukee, Wis.

[*] Notice: The term of this patent shall not extend beyond the expiration date of Pat. No. 5,371,241.

[21] Appl. No.: 348,707

[22] Filed: Dec. 2, 1994

Related U.S. Application Data

[63] Continuation-in-part of Ser. No. 732,548, Jul. 19, 1991, Pat. No. 5,371,241.

[51] Int. Cl.⁶ .................... C07D 311/78; A61K 31/335
[52] U.S. Cl. .................... 549/220; 549/223; 549/225; 536/24.3
[58] Field of Search .................... 549/220, 223, 549/225; 536/24.5, 24.3

[56] References Cited

U.S. PATENT DOCUMENTS 4,762,779  8/1988  Snitman .................... 435/6

FOREIGN PATENT DOCUMENTS

| | | |
|---|---|---|
| 0251786 | 1/1988 | European Pat. Off. . |
| 0252683 | 1/1988 | European Pat. Off. . |
| 0323152 | 7/1989 | European Pat. Off. . |
| 0359225 | 3/1990 | European Pat. Off. . |
| WO91/17169 | 11/1991 | WIPO . |

OTHER PUBLICATIONS

Schubert, et al., *Nucl. Acids Res.* 18[11]:3427 (1990).
Trainor, et al., "Chemical Reagents for Molecular Biology", Apr. 6, 1989 (Abstract).
Roget, et al., *Nucl. Acids Res.* 17[19]:7643–7651 (1989).
Alves, et al., *Tetrahedron Letters* 30[23]:3089–3092 (1989).
Bannwarth, et al., *Tetrahedron Letters* 30[12]:1513–1516 (1989).
Misiura, et al., *Nucl. Acids Res.* 18[15]:4345–4345 (1990).
"TFA Aminolinker Amidite", Pharmacia LKB Biotechnology advertisement.
"AutoPrimer Synthesis Kit Instructions", booklet from Pharmacia LKB Biotechnology (1990).
Haralambidis, et al., *Tetrahedron Letters* 28[43]:5199–5202 (1987).
Pieles, et al., *Nucl. Acids Res.* 18[15]:4355–4360 (1990).
Haugland, *Handbook of Fluorescent Probes and Research Chemicals*, pp. 30–32, 34–36 (1989).
Smith, et al., *Nature* 321:674–679 (1986).
Ansorge, et al., *Nucl. Acids Res.* 15[11]:4593–4602 (1987).
Kaiser, et al., *Nucl. Acids Res.* 17[15]:6087–6102 (1989).
Voss, et al., *Nucl. Acids Res.* 17[7]:2517–2527 (1989).
Ansorge, et al., *J. Biochem. & Biophys. Meth.* 13:315–323 (1986).
Schulhof, et al., *Nucl. Acids Res.* 15[2]:397–416 (1987).
*Abstracts of Papers* (Part 1), Abstract No. 35, 203rd American Chemical Society National Meeting, Apr. 1992.
Millipore Product Bulletin for FluorDite, May 1993.
P. 118 from 1993–1994 Applied Biosystems catalog showing FAM Amidite.
Cohen, et al., "Use of phosphoramidite–linked acridine for fluroescent tagging of oligo–deoxy–nucleotides", Derwent World Patents Index Accession No. 89–129850/17 (1989).
"TFA Aminolinker Amidite", Pharmacia LKB Biotechnology advertisement (Nov. 1990).

*Primary Examiner*—Gary L. Kunz
*Attorney, Agent, or Firm*—Quarles & Brady

[57] ABSTRACT

Compounds useful to attach a fluorescein label to an oligonucleotide are disclosed. To create these compounds, oxygen groups on the fluorescein moiety are protected (e.g. with acyl groups). One then links a phosphoramidite to the fluorescein moiety via an amide or thiourea linkage to an active site on the fluorescein ring. The resulting compound can then be directly linked to an oligonucleotide as it is being formed in an automated synthesizer and then deprotected using the same deprotection conditions as are used to deprotect the oligonucleotides. Such compounds are, inter alia, useful to create labelled primers for DNA sequencing.

4 Claims, 5 Drawing Sheets

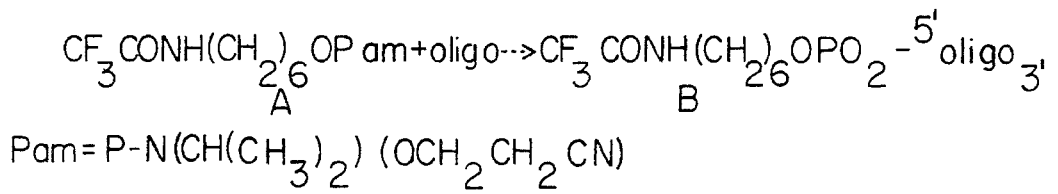
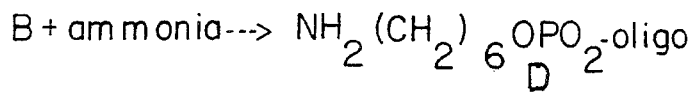
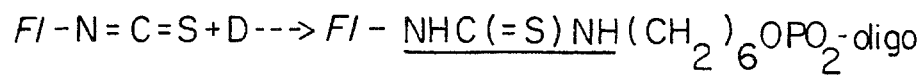
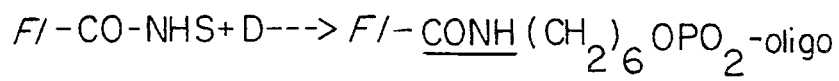
Fl = fluorescein
FIG.1
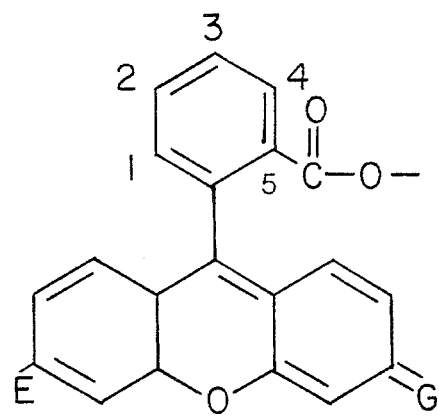
OR
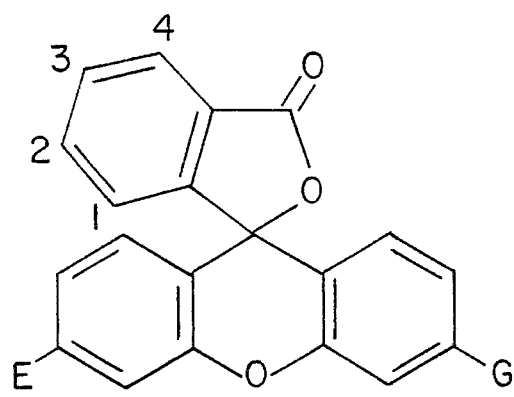
FIG.2

FLUORESCEIN LABELLED PHOSPHORAMIDITES

This application is a continuation-in-part of application Ser. No. 07/732,548 filed Jul. 19, 1991 now U.S. Pat. No. 5,371,241.

FIELD OF THE INVENTION

This invention relates to fluorescein labelled compounds that are useful in the production of fluorescently labelled oligonucleotides (e.g. fluorescently labelled primers for automated DNA sequencing).

BACKGROUND OF THE INVENTION

DNA sequencing can now be performed automatically by machine. See generally, W. Ansorge, et al., 13 *J. Biochem. Biophys. Methods* 315–323 (1986). The disclosures of this publication and the disclosures of all other publications recited herein are incorporated by reference as if fully set forth herein.

One type of commercially available machine for automated sequencing is the A.L.F. DNA Sequencer, sold by Pharmacia LKB Biotechnology. This sequencer uses a primer, which is a small oligonucleotide of known sequence. The primer hybridizes to a section of a DNA molecule that is to be sequenced and thereby creates a short double-stranded region that enables DNA polymerase to replicate the single-stranded portion of the DNA. In accordance with the Sanger dideoxy sequencing method, four types of dideoxy terminators are separately added during synthesis to create different length fragments, and these fragments are then separated on a gel by length. The gel positions of the fragments provide sequence information.

This method of automated sequencing relies on the addition of labels to the primer so that after separation on the gel the position of the labels can automatically be read by the machine. Labelled primers include those with fluorescent, bioreactive, chemiluminescent, or photolabile labels.

Labels have usually been attached to an oligonucleotide in a multi-step procedure. The first step requires synthesis of an oligonucleotide bearing a protected amine by attaching a protected phosphoramidite/linker to the oligonucleotide. Then, the resulting compound is deprotected. After that, the compound is linked to a fluorescent label.

This procedure requires partial purification of the deprotected oligonucleotide, reaction with the label, removal of the excess reagent, and then purification of the labelled oligonucleotide. The overall process is tedious, and usually requires two days to produce a labelled oligonucleotide. Additionally, there are yield losses at each step in the multi-step process. Further, this work must normally be done by the user of the automated sequencer since the user usually wants to custom design an appropriate short nucleotide to prime a sequence of interest.

To avoid these problems, the art prepared label-linked phosphoramidites which could later be reacted with oligonucleotides. Amidites linked to a chemically inert bathophenanthroline-ruthenium complex, W. Bannwarth, et al., 30 *Tet. Let.* 1513–1516 (1989) have been prepared. Biotin-containing amidites have also been prepared. A. Alves, et al., 30 *Tet. Let.* 3089–3092 (1989). Also, amidites linked to dinitrophenyl, dansyl, and pyrenyl labels have been prepared. A. Roget, et al., 17 *Nuc. Acids Res.* 7643–7651 (1989). European Patent Application 89116946.8 (Publication No. 359,255) discloses a xanthene dye-linked amidite.

However, fluoresceins are highly preferred labels. They have exceptionally high fluorescent emission/mol, excellent solubility, relatively low cost, and other useful characteristics. F. Schubert, et al., 18 *Nucl. Acids Res.* 3427 (1990) attempted the synthesis of a phosphoramidite linked to fluorescein, albeit through one of the fluorescein phenolic hydroxyls. Unfortunately, this approach significantly reduced fluorescence and shifted absorption and emission wavelengths from desired regions.

Thus, the normally used method to obtain fluorescein labelled oligonucleotides still is the multistep approach, an example of which is described in FIG. 1. Addition of linker phosphoramidite A to the 5' end of an oligonucleotide on a DNA synthesizer yields B. After deprotection and desalting of B to yield D, the active nucleophile in D reacts with fluorescein isothiocyanate or carboxyfluorescein, N-hydroxysuccinimide (NHS) ester to yield a labelled oligonucleotide in which fluorescein is bound to the oligonucleotide through a thiourea or amide group and a six carbon linker. This procedure suffers from the problems described above for multi-step approaches, but yields a product with the characteristic fluorescein absorption and emission wavelengths.

Complicating matters is the fact that fluorescein has two active oxygen sites that when unprotected will interfere with a phosphoramidite attempting to link to fluorescein. Moreover, linkages to phosphoramidites can be adversely affected by deprotection conditions used for many protecting groups. Also, many conditions will affect or cause a reaction with a carboxyl group on the fluorescein ring.

As such, a need exists for labelled fluorescein phosphoramidites having good stability characteristics, which can readily be synthesized at high yields, and which confer high fluorescent emission/mol at desired wavelengths when linked to oligonucleotides.

SUMMARY OF THE INVENTION

In one aspect, the invention provides a compound of the following formula:

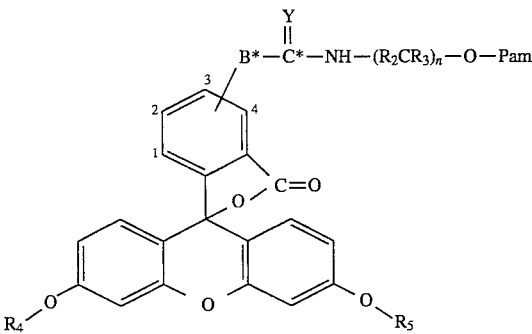

wherein the substituent

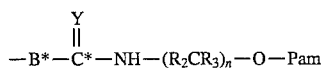

is linked to the fluorescein carbon 1, 2, 3, or 4 positions at B*, or when B* is absent at C*; B* is selected from the group consisting of $NR_1$, O, S, and nothing; $R_1$, $R_2$ and $R_3$ are selected from the group consisting of alkyl groups having 6 or less carbons and H; C*=Y is selected from the group consisting of C=O and C=S, and, when B* is absent, $CH_2$; n is a number selected from the group 2–12; and Pam is a phosphoramidite. The carbon numbering/lettering is as specified in FIG. 2. Oxygens at the E and G positions in the fluorescein moiety are preferably protected by $R_4$ and $R_5$ each of which may be acyl groups, or other groups that are of the type that are readily removable by treatment with ammonia, such as groups of the structure $CH_2CH_2X$, where X is an electron-withdrawing moiety. Examples of such groups are $CH_2CH_2CN$ and $CH_2CH_2SO_2\phi$. $R_4$ and $R_5$ are preferably isobutyryl or pivaloyl groups.

In a preferred form, B* can be NH, C*=Y can be C=S, n can be 6, Pam can be a N,N-diisopropyl-beta-cyanoethylphosphoramidite, $R_2$ and $R_3$ can be H, and the substituent can be linked at the fluorescein carbon 3.

In another preferred form, B* is absent, C*=Y can be C=O, n can be 6, Pam can be a N,N-diisopropyl-beta-cyanoethyl-phosphoramidite, $R_2$ and $R_3$ can be H, and the substituent can be linked at the fluorescein carbon 3 and/or 4.

In yet another aspect, the invention provides a method of attaching a fluorescein label to an oligonucleotide. One reacts one of the compounds of the present invention with an oligonucleotide such that the label becomes linked to the oligonucleotide.

An object of the present invention is therefore to provide a compound useful in fluorescently labelling an oligonucleotide.

Another object is to provide a method of labelling oligonucleotide where the technician merely has to add a compound of the present invention to an oligonucleotide in an automated DNA synthesis machine.

Yet another object of the present invention is to link a label of the above kind to an oligonucleotide in such a way that the labelled oligonucleotide is stable, and in a way that preserves the fluorescein E and G oxygen groups and thus the wavelength characteristics of fluorescein.

Yet another object of the present invention is to use thiourea and amide linkages to connect fluorescein to a phosphoramidite.

The foregoing and other objects and advantages of the invention will appear from the following description. In the description, reference is made to the accompanying drawings which form a part hereof and in which there is shown by way of illustration preferred embodiments of the invention. Such embodiments do not necessarily represent the full scope of the invention. Thus, reference must be made therefore to the claims herein for interpreting the scope of the invention.

BRIEF DESCRIPTION OF THE DRAWINGS

FIG. 1 is a schematic diagram of a prior art multi-step procedure for labelling an oligonucleotide with fluorescein;

FIG. 2 depicts two core structures of fluorescein moieties;

DESCRIPTION OF THE PREFERRED EMBODIMENTS

"Fluorescein moieties" are those having either of the FIG. 2 cores. The E and G substitutions are either =O or —O—R (with R being various atoms or groups such as H, Na, and acyl or other protecting groups). Fluorescein moieties may also include substitutions for H, such as $NH_2$, $—NH_2=C=S$, SR, $NO_2$, OR, $SO_2$ or —COOH on other than the xanthene portion of the molecule.

A problem that had to be overcome is that unprotected E and G oxygens will interfere with phosphoramidite linkage. Thus, one must provide reversible protection for these groups and a linkage to fluorescein that can survive deprotection conditions, while not interfering with emission. It has been discovered that suitable protecting groups are acyl groups such as the isobutyryl group used in Example B, the acetyl group used in Example A, and other groups that can be removed by treatment with ammonia.

The linker of the present invention is connected at fluorescein carbons 1, 2, 3, or 4 of the fluorescein structure (preferably at 3 or 4). A preferred linker segment is:

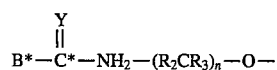

with n between 2 and 12 (preferably 6); C*=Y either C=S, C=O or, if B* is nothing, $CH_2$; and B* being. $NR_1$, O, S, or nothing (preferably nothing). The linker is in turn connected to a phosphoramidite group.

The overall synthesis approach for compounds of this type is to first create a fluorescein in which the E and G positions are protected (e.g. by acyl group moieties), and the fluorescein has a nitrogen, carbon, sulfur, or oxygen atom substituted at the 1, 2, 3 or 4 carbon positions. This is typically done by introducing active sites on that ring before linking that ring to the other fluorescein rings during synthesis of fluorescein. Various compounds of this type are already commercially available. A linker is then added that has the $(R_2CR_3)_n$—O—H terminus. For example, it has been learned that the addition of an amine to yield an amide group or thiourea group can be performed in high yield without affecting the carboxyl group or fluorescein. Then, the phosphoramidite is connected to the linker via a condensation reaction.

EXAMPLE A

An Amidite Derived from Fluorescein Isothiocyanate

Figure 3:
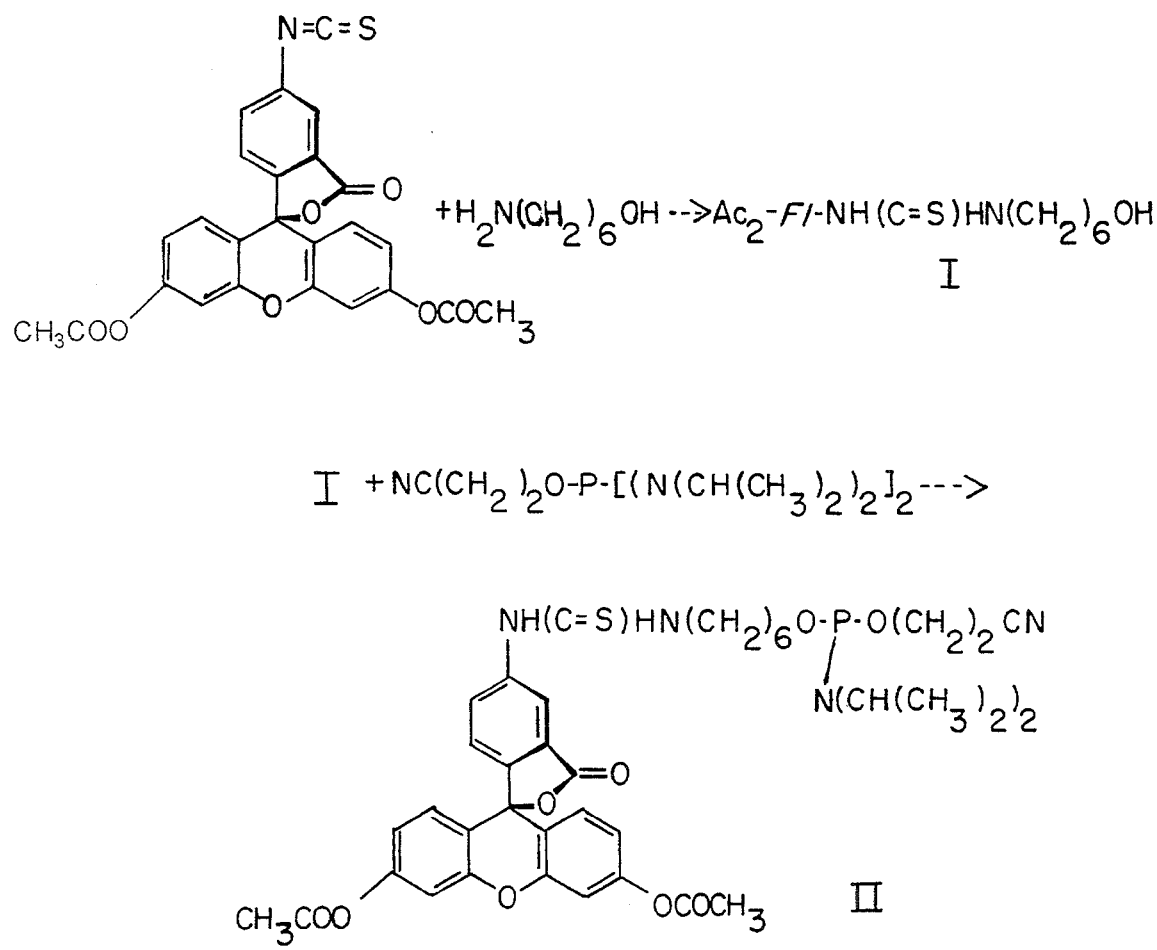
FIG. 3 is a flow diagram of the preparation of an embodiment of the present invention disclosed in Example A.

Referring to FIG. 3, commercially available fluorescein 3-isothiocyanate diacetate was treated with one equivalent of aminohexan-6-(ol) to yield I. Reaction of I with a phosphitylating reagent yielded II, a phosphoramidite linked to fluorescein via a six carbon chain and thiourea group. This labelled phosphoramidite can be reacted with an oligonucleotide on a DNA synthesizer. The resulting fluorescein-labelled oligonucleotide may be used as a primer in automated DNA sequencing, and the linkage will survive deprotection of the fluorescein and oligonucleotide.

Compound I

Fluorescein 3-isothiocyanate diacetate (40 mg, 0.084 mmol) was suspended in dry DMF. Aminohexan-6-ol (11.8 mg, 0.1 mmol) in absolute ethanol was added to the DMF solution. After 1.5 hours the reaction was complete and Compound I was formed, as indicated by TLC analysis. The solvents were evaporated and the residue dissolved in chloroform, filtered, extracted with water, dried, and evaporated. Compound I was dried by co-evaporation with dry dichloromethane. The product, Compound I, was purified by preparative TLC. Yield: 41 mg (83%).

Compound II

Tetrazole (2.5 mg, 0.035 mmol) and diisopropylethylamine (5 μL, 0.035 mmol) were added in dichloromethane to the residue under dry nitrogen. Bis-(N, N-diisopropyl)-Beta-cyanoethyl phosphordiamidite (24 μL, 0.077 mmol) was added and the reaction was stirred for two hours. The solvent was evaporated and the residue dissolved in ethyl acetate, extracted with cold 10% sodium carbonate solution, dried, and evaporated. The residue (32 mg, 58%) was analyzed by HPLC and found to contain 80% of the expected Compound II amidite via analysis (by C-18 HPLC with diode array UV detection).

Synthesis of a Fluorescein-linked Oligonucleotide

Compound II was dissolved in dry acetonitrile at a concentration of 0.1M. The solution was placed on port 6 of a Pharmacia Gene Assembler Plus and used to prepare a labelled primer for the site 40 bases upstream from the multiple cloning site in the M13mp series of single stranded cloning vectors. Compound II was added as the final step of oligonucleotide synthesis, which was performed as noted in FIG. 4. Basically, the 5'- OH on the deoxyribose of a nucleotide reacts at the phosphoramidite phosphorus, causing the amine to leave. That phosphorus is then oxidized, and the labelled oligonucleotide is then deprotected with concentrated ammonia for 30 minutes at 70° C. Compare J. Schulfhof, et al., 15 *Nuc. Acid. Res.* 397–416 (1987) (deprotection with ammonia of oligonucleotides). The ammonia solution is passed through a NAP 10 gel filtration column and the eluant is evaporated to dryness. The product is redissolved in water and purified by C-18 HPLC (gradient: 5%–25% acetonitrile/0.1M TEAA, pH 7, 20 minutes). The product peak was collected and repurified by the same system.

Figure 4:
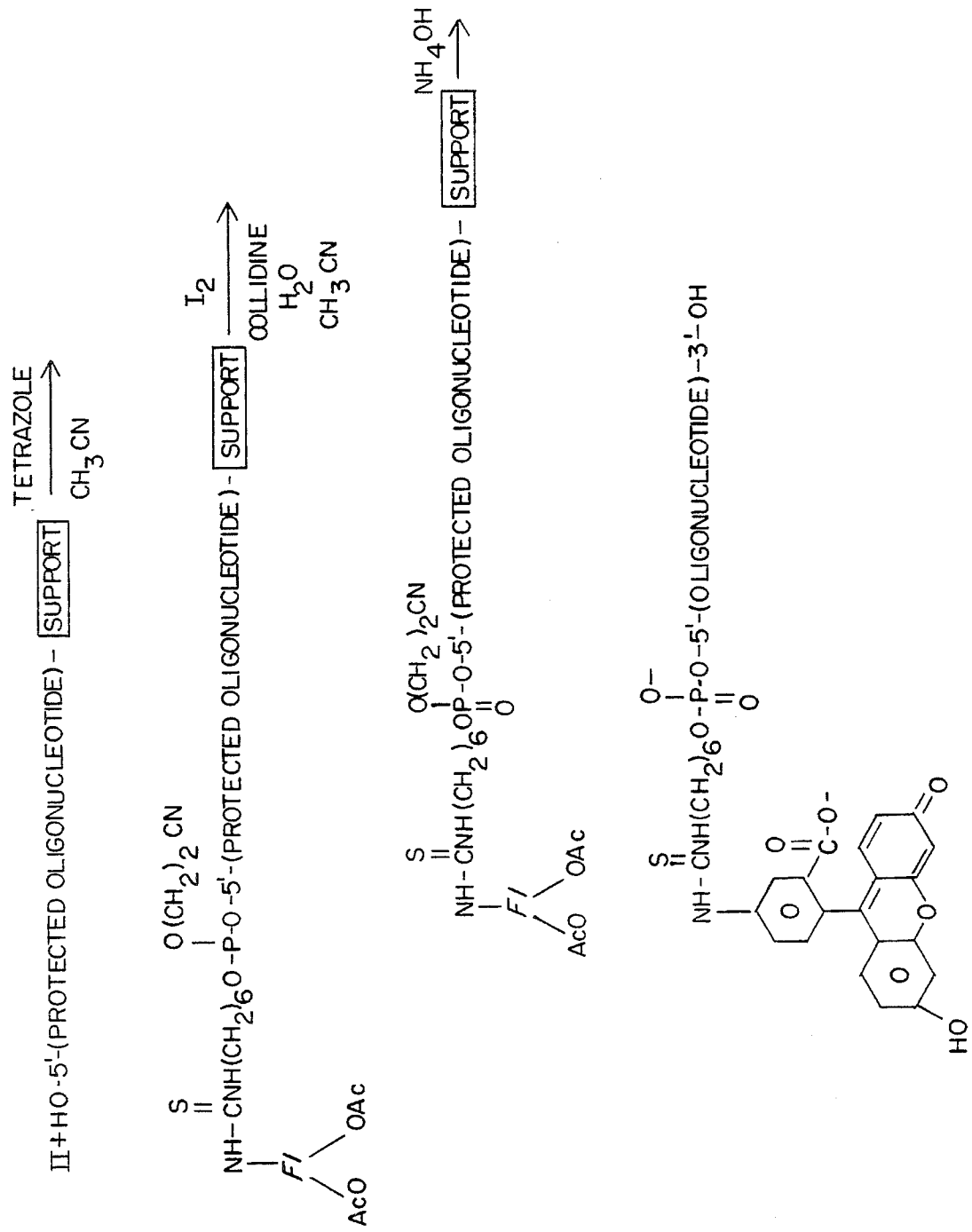
FIG. 4 is a flow diagram of the preparation of a labelled oligonucleotide using Compound II of FIG. 3.

The following are conditions for linking an amidite to an oligonucleotide (see FIG. 4). At the 5'-end of a support-bound oligonucleotide prepared on a DNA synthesizer, the protecting dimethoxytrityl group is removed by brief treatment with dichloro or trichloroacetic acid, freeing the 5' hydroxyl. After washes with dichlorethane and acetonitrile, the fluorescein amidite is delivered to the support with tetrazole catalyst in acetonitrile. The activated amidite reacts with the 5'-OH to yield a phosphite triester, which is oxidized to a phosphate triester by a mixture of iodine, collidine and water. After washing with acetonitrile, the labelled oligonucleotide is treated with ammonium hydroxide to remove the protecting groups. The final sequence of the labelled oligonucleotide is: unprotected fluorescein—NH(C=S)NH(CH$_2$)$_6$—O—PO$_2$—O-d(CGC-CAGGGTTTTCCCAGTCACGAC).

The fluorescein-linked primer was then used under standard sequencing conditions on an automated laser fluorescence DNA sequencer (A.L.F. machine, Pharmacia LKB). See generally W. Ansorge, et al. 15 *Nucl. Acids Res.* 4593 (1987); L. Smith, et al. 321 *Nature* 674 (1986). The fluorescein-linked primer performed as well as the identical primer made by the FIG. 1 prior art procedure.

EXAMPLE B

An Amidite Derived from Fluorescein 3(4) Carboxylic Acid

Figure 5:
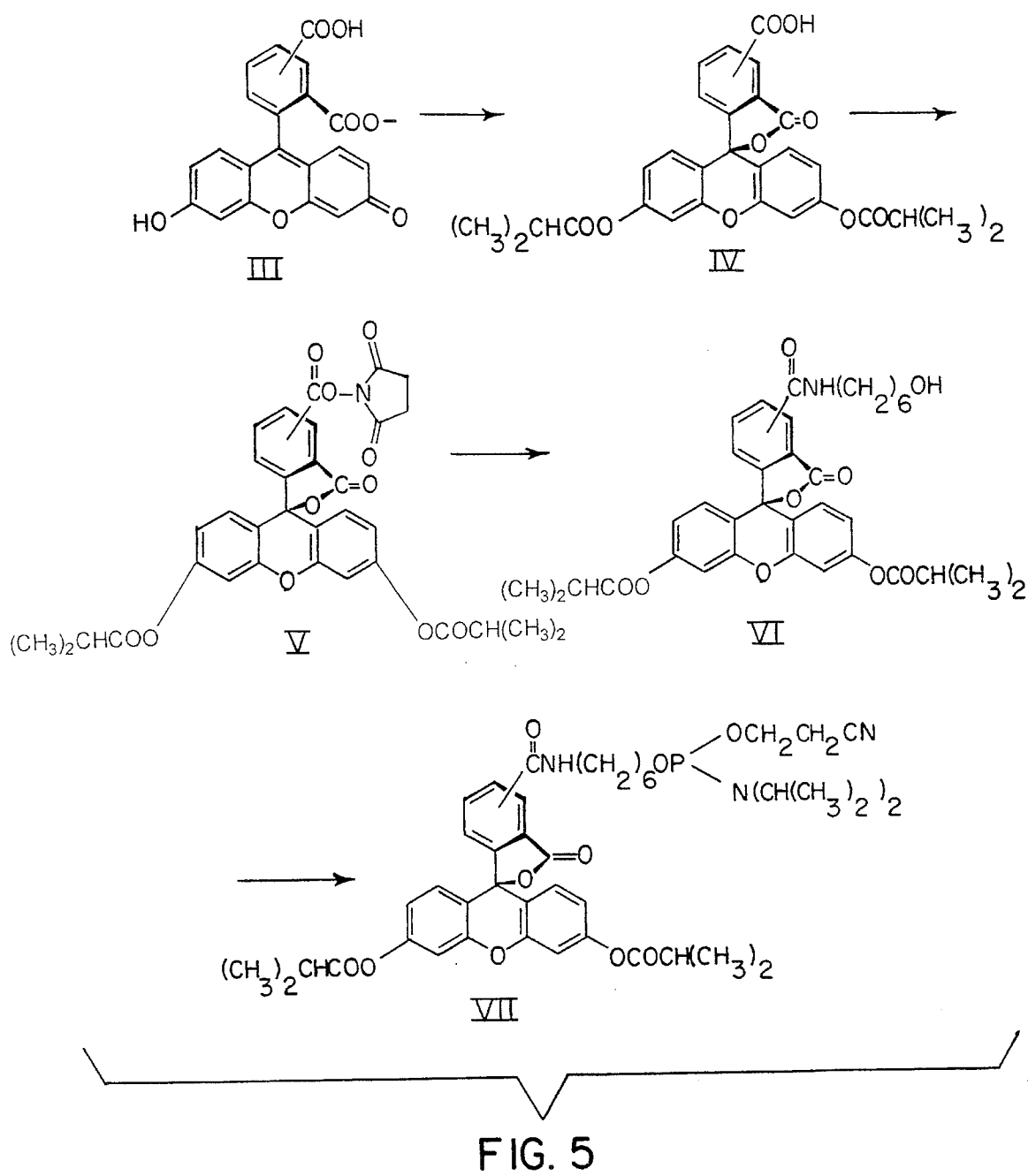
FIG. 5 is a flow diagram of the preparation of the embodiment of the present invention disclosed in Example B.
Figure 6:
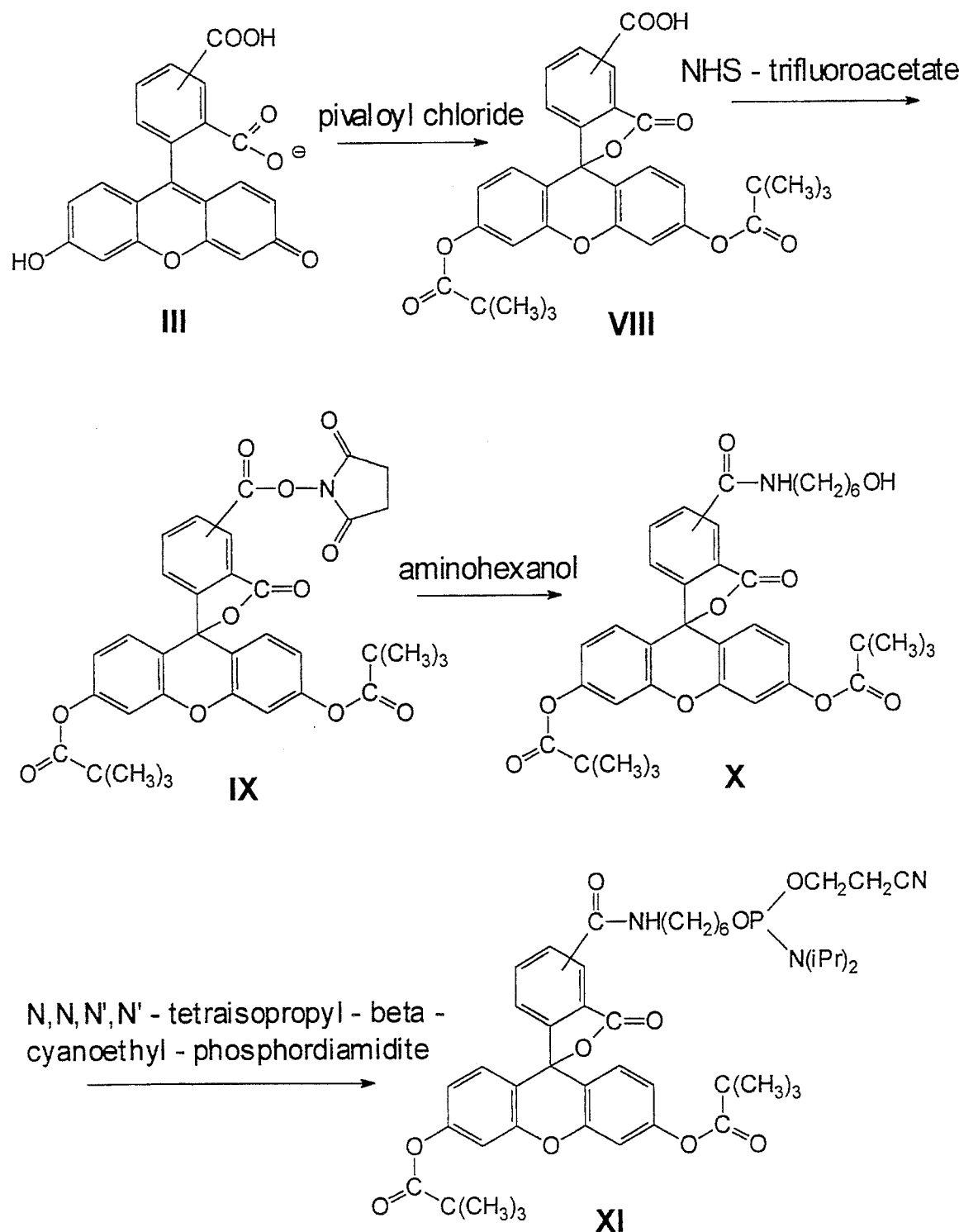
FIG. 6 is a flow diagram of the preparation of the embodiment of the present invention disclosed in Example C.

Referring to FIG. 5, fluorescein 3(4) carboxylic acid (a mixture thereof) (III) was converted by treatment with isobutyryl chloride to its protected di-isobutyryl ester form (IV). Compound IV was then treated with N-hydroxysuccinimide to form an active ester (V), then treated with aminohexan-6-ol to yield Compound VI. Phosphitylation, as described in Example A, provided the fluorescein amidite VII in good yield. The amidite was used as described above to prepare a fluorescein labelled oligonucleotide which gave results comparable to a primer made by the multi-step procedure.

Compound IV

Fluorescein 3(4)-carboxylic acid (90% pure, 106 g, 0.282 mol) was dissolved in 800 mL dry pyridine, followed by the addition of 140 mL (1.39 mol) of dry diisopropylethylamine. The mixture was cooled to 0° C. and isobutyryl chloride (70 mL, 71.2 g, 0.69 mol) was added. The reaction was complete by the end of the addition and Compound IV was formed.

The completed reaction mixture was concentrated to a gum on a rotovap, dissolved in 2 L of dichloromethane and extracted three times with 2 L of water. The organic layer was dried with sodium sulfate and evaporated to a crusty solid. The residue was evacuated at high vacuum overnight, then chromatographed on a 10 L silica gel preparative HPLC column using a gradient of 0–5%, then 10% methanol in chloroform. Yield: 108.2 g (74.5%) of an amorphous solid, purity of 98.6% of HPLC (mixture of isomers). Identity confirmed by $^1$H NMR, UV.

Compound V

Compound IV (108 g, 0.21 mol) was placed in a 3 L round bottom flask with 1200 mL of dichloromethane. Dry pyridine (40 mL) was added, the flask capped with a drying tube, and the mixture stirred until complete dissolution. Disuccinimidyl sulfite (75 g, 0.27 mol) was added to the reaction mixture. The reaction was completed after 15 min. The solvent was evaporated and the residue coevaporated twice with toluene. The mixture was purified by chromatography on a silica gel preparative HPLC column using chloroform as the eluant. Yield: 90 g (68%). HPLC purity: 93.5%. The impurities were identified by separation of enriched column fractions by preparative TLC and identified by $^1$NMR as a mixture of both isomers of the methyl and ethyl esters. Identity: $^1$H NMR, UV.

Compound VI

Compound V (86.4 g, 0.137 mol) was dissolved in 1000 mL of dichloromethane and aminohexan-6-ol (29 g, 0.246 mol). 600 mL of dichloromethane was added dropwise to the reaction mixture over a period of 1 hr. After one additional hour, the reaction mixture was filtered and the solid washed with 300 mL of dichloromethane. The filtrate was concentrated to 1 L and extracted once with 1 L of water, dried with sodium sulfate, and evaporated. The residue was chromatographed on a 4 L silica preparative HPLC column, with a step gradient of 0%, 1%, 1.5%, and 2% methanol in chloroform to yield 55.6 g (65.3%) of the product as a mixture of isomers. Purity by HPLC: 97%. Identity: $^1$H NMR, UV.

Compound VII

Diisopropylamine (5.47 mL, 3.95 g, 0.039 mol) and tetrazole (2.72 g, 0.039 mol) were added to 300 mL of dry acetonitrile in a 1 L round bottom flask. The flask was swept with argon and a drying tube was inserted. After the reaction had been stirred for 15 min., Compound VI (49.0 g, 0.0776 mol), dissolved in 300 mL of dry acetonitrile, was added. After further purging with argon, 32 mL (30.4 g, 0.101 mol) of bis-(N,N-diisopropyl)-Beta-cyanoethylphosphordiamidite was added dropwise to the mixture. The reaction was complete after one hour and compound VII was formed.

The reaction was filtered and the filtrate concentrated to a gum on a rotovap. The residue was filtered and chromatographed on a column of 1 L of silica gel with 1:1 dichloromethane/ethyl acetate as the solvent. The appropriate fractions, eluting near the solvent front, were collected, pooled and evaporated. The residue was pumped under high vacuum until a glassy foam was obtained. Yield: 40 g, 63%. Purity by HPLC: 93%. Identity: $^1$H NMR, UV.

Fluorescein-linked Oligonucleotide

Compound VII was dissolved in dry acetonitrile as described above and used in reactions as described above to prepare a labelled oligonucleotide. This labelled oligonucleotide was employed in automated DNA sequencing. As in Example A, the sequencing results were identical to those obtained when using oligonucleotides labelled by the multistep synthetic procedure described above.

EXAMPLE C

Pivaloyl Protected Fluorescein Amidite

Synthesis of 3(4)-Carboxyfluorescein dipivalate (Compound VIII)

In a 100 mL round bottom flask in an H$_2$O ice bath on a magnetic stir plate, 5.08 g (0.0135 mol) of 3(4)-carboxyfluorescein (a mixture thereof) was added, followed by 35 mL of dry pyridine and 3.7 mL triethylamine (TEA). When the temperature of the reaction mixture reached approximately 6° C., 3 equivalents (5.0 mL) of pivaloyl chloride were added by pipette. The reaction proceeded to 21 hours, the ice melting and the bath attaining room temperature. Additional pivaloyl chloride may be added if necessary.

The solvent was evaporated and the residue dissolved in 50 mL dichloromethane and extracted with dilute HCl, pH 3.0. The organic layer was separated and dried with sodium sulfate. It was evaporated to dryness, placed on a vacuum pump overnight, then stored at −20° C. The product was chromatographed on flash silica with dichloromethane, followed by a step gradient of isopropanol/dichloromethane. The appropriate fractions were collected and evaporated to dryness.

Synthesis of 3(4)-Carboxyfluorescein dipivaloyl-N-succinimidyl ester (Compound IX)

N-hydroxysuccinimidyl trifluoroacetate was prepared in a dry 50 mL flask, to which 0.61 g of N-hydroxysuccinimide was added. Three equivalents (3.3 mL) of trifluoroacetic anhydride were added and the reaction mixture kept under argon. After all the solid dissolved the mixture was evaporated to an oil, then pumped dry. Yield: 1.1 g.

To a 100 mL round bottom flask was added 1.57 g (0.002883 mol) of 3(4)-carboxyfluorescein dipivalate. It was dissolved in 17 mL of dry dichloromethane and 1.2 mL of dry pyridine and 1.8 equivalents (1.11 g) of N-hydroxysuccinimidyl trifluoroacetate were added. After 1.5 hours, the mixture was evaporated to an oil. The residue was partitioned between 0.001M HCl and dichloromethane. The organic phase was separated, dried with sodium sulfate and evaporated to an oil. It was used without any further purification.

Synthesis of Fluorescein dipivaloyl-3(4)-(N-(6'-hydroxyhexyl))-carboxamide (Compound X)

3(4)-Carboxyfluorescein dipivaloyl-N-succinimidyl ester (1.49 g (0.002322 mol)), was dissolved in 15 mL of dry dichloromethane. The flask was flushed with argon. 6-aminohexanol (0.95 equivalents (258 mg)) in 15 mL dry dichloromethane was added dropwise over a period of half an hour. The residue was partitioned between water and dichloromethane. The organic phase was separated, dried with sodium sulfate and evaporated to an oil.

The residue was chromatographed on flash silica with dichloromethane using a step gradient of isopropanol. The appropriate fractions were pooled, evaporated to an oil, used to prepare the amidite.

Synthesis of Fluorescein dipivaloyl amidite (Compound XI)

Tetrazole (21.2 mg) and 42.5 μL of diisopropylamine were placed in a dry round bottom flask. Dry acetonitrile (2.4 mL) was added, the flask flushed with argon and the mixture stirred for 20 minutes. The purified hexanol derivative of fluorescein (0.4 g, 0.000606 mol) was added in 2.4 mL of dry acetonitrile. N,N,N',N'-tetraisopropyl-β-cyanoethyl phosphordiamidite (0.95 equivalents, 250 μL) was added to the reaction mixture. After 30 minutes, the reaction mixture was concentrated to a solid and placed on a vacuum pump to dry. The product was purified by chromatography on 26 g of silica gel 60 and eluted with 1:1 ethyl acetate and dichloromethane. After the appropriate fractions were pooled and evaporated to an oil, the product was triturated once with ether. The remaining ether was evaporated and the product was dissolved in dichloromethane, washed once with water, and dried with sodium sulfate. The solvent was evaporated and the product stored at −20° C.

Test of Fluorescein dipivaloyl Amidite on DNA Synthesizer

The amidite was dissolved in dry acetonitrile and coupled to the end of T$_{15}$ on an automated DNA synthesizer using standard conditions. The labeled oligonucleotide was deprotected in ammonium hydroxide and analyzed by C18 reverse phase HPLC. The expected fluorescein-T15 oligonucleotide (Compound XII) was detected as approximately 60% of the mixture.

The following table presents analytical data for the compounds of Example C:

|  | HPLC (retention time, min.) | % purity | UV-vis($\lambda_{max}$) | $^1$H NMR |
|---|---|---|---|---|
| 3,(4)-carboxyfluorescein dipivalate (VIII) | 7.14, 7.39 | 78 | 228, 233, 290 (sh) |  |
| 3,(4)- | 11.91, 12.39 | 95 | 224, 290 (sh) | 1.3(s, piv), 3.0(s, NHS), 6.8–8.8 |

-continued

| | HPLC (retention time, min.) | % purity | UV-vis($\lambda_{max}$) | $^1$H NMR |
|---|---|---|---|---|
| carboxyfluorescein dipivalate NHS ester (IX) | | | | (m, aromatic) |
| 3,(4)-carboxyfluorescein dipivalate hyroxyhexyl carboxamide (X) | 10.78, 11, 10 | 74 | 219, 224, 290 (sh) | 1.4(s, piv), 1.6(m, (CH$_2$)$_4$), 3.3–3.7(m, X—CH$_2$), 6.8–8.8(m, aromatic) |
| 3,(4)-carboxyfluoresceing dipivalate hydroxyhexyl carboxamide phosphoramidite (XI) | 10.33, 10.69 | 42 | 219, 285 (sh) | 1.2(m, iPr), 1.3(s, piv), 1.6(m. (CH$_2$)$_4$), 2.7(m, CH$_2$CN), 3.4–4.0(m, X—CH$_2$), 6.8–8.8(m, aromatic) |
| 5'-fluorescein-T$_{15}$ (XII) | 10.2, 11.06 | 62 | 240, 271, 491 | |

Many modifications and variations of the preferred embodiments are possible without deviating from the spirit and scope of the invention. For example, by starting with fluoresceins that have —S— substitutions at the 1, 2, 3, or 4 positions, similar strategies can be used to provide compounds where B is S. For example, fluorescein with an available amino group attached to carbon 1, 2, 3 or 4 can be reacted with HNO$_2$ and RSS$^-$ to form fluorescein with a SSR group substituted for the amino group. This compound is reacted with pyridine and R—(C=O)—Cl to form a protected compound. Treatment of the protected compound with DTT yields a protected compound with an SH group in place of the SSR group. The SH group can then react to form a linker.

Various other phosphoramidites, such as those disclosed in PCT application WO86/07362, are also intended as "Pam". Thus, applicant's invention is not to be limited to just the examples shown.

I claim:

1. A compound of the following formula:

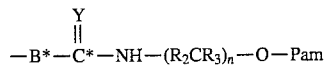

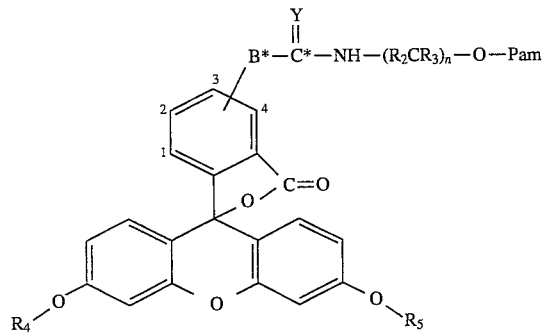

wherein: the substituent $$-B^*-C^*-NH-(R_2CR_3)_n-O-Pam$$
       $\overset{Y}{\|}$ is linked to the carbon 1, 2, 3, or 4 positions at B*, or when B* is absent at C*;

B* is selected from the group consisting of NR$_1$, O, and S, or B* is absent;

C*=Y is selected from the group consisting of C=O, C=S and, when B* is absent, CH$_2$;

R$_1$, R$_2$, and R$_3$ are hydrogen or an alkyl group possessing 1 to 6 carbon atoms;

R$_4$ and R$_5$ each is a pivaloyl group;

n is an integer from 2 to 12; and

Pam is a N,N-diisopropyl-beta-cyanoethyl phosphoramidite.

2. The compound of claim 1, wherein the carbon 1, 2, 3, or 4 position is linked to (R$_2$CR$_3$)$_n$ by a thiourea linkage where B* is NR$_1$, and C*=Y is C=S, or an amide linkage where B* is absent and C*=Y is C=O.

3. The compound of claim 1, wherein B* is NH, C*=Y is C=S, R$_1$, R$_2$, and R$_3$ are H, and n is 6.

4. The compound of claim 1, wherein B* is absent, C*=Y is C=O, R$_1$, R$_2$, and R$_3$ are H, and n is 6.

* * * * *